(12) United States Patent
Beumer et al.

(10) Patent No.: US 8,586,349 B2
(45) Date of Patent: Nov. 19, 2013

(54) MOVING DROPLET DIAGNOSTIC ASSAY

(75) Inventors: Thomas Augustinus Maria Beumer, Oss (NL); Petrus Franciscus Hendrikus M. Verheijden, Eersel (NL); Hendrik Sibolt van Damme, Hertogenbosch (NL)

(73) Assignee: Biomerieux B.V., Boxtel (NL)

( * ) Notice: Subject to any disclaimer, the term of this patent is extended or adjusted under 35 U.S.C. 154(b) by 595 days.

(21) Appl. No.: 10/344,226

(22) PCT Filed: Aug. 6, 2001

(86) PCT No.: PCT/EP01/09073
§ 371 (c)(1), (2), (4) Date: Aug. 1, 2003

(87) PCT Pub. No.: WO02/12895
PCT Pub. Date: Feb. 14, 2002

(65) Prior Publication Data
US 2004/0043421 A1    Mar. 4, 2004

(30) Foreign Application Priority Data
Aug. 10, 2000    (EP) .................................. 00202811

(51) Int. Cl.
G01N 33/00 (2006.01)
G01N 33/53 (2006.01)
C12Q 1/00 (2006.01)
C12Q 1/68 (2006.01)
D21C 3/00 (2006.01)

(52) U.S. Cl.
USPC ............ 435/287.1; 435/4; 435/6.19; 435/7.1; 435/7.92; 435/39; 435/287.2; 436/176; 436/501; 436/536

(58) Field of Classification Search
USPC ............ 422/55, 56, 57, 58, 61, 68.1; 435/7.2, 435/283.1, 286.5, 287.1, 287.2, 287.9, 435/288.5, 288.7; 436/517, 518, 523, 536
See application file for complete search history.

(56) References Cited

U.S. PATENT DOCUMENTS

| | | | |
|---|---|---|---|
| 4,313,734 A | 2/1982 | Leuvering | |
| 4,373,932 A | 2/1983 | Gribnau et al. | |
| 4,632,901 A | 12/1986 | Valkirs et al. | |
| 4,703,017 A | 10/1987 | Campbell et al. | |
| 4,920,046 A | 4/1990 | McFarland et al. | |
| 5,304,487 A * | 4/1994 | Wilding et al. | 435/29 |
| 5,637,469 A * | 6/1997 | Wilding et al. | 435/7.21 |
| 5,726,026 A * | 3/1998 | Wilding et al. | 435/7.21 |
| 5,773,234 A * | 6/1998 | Pronovost et al. | 435/7.36 |
| 5,842,787 A * | 12/1998 | Kopf-Sill et al. | 366/340 |
| 5,866,345 A * | 2/1999 | Wilding et al. | 435/7.21 |
| 6,046,056 A * | 4/2000 | Parce et al. | 506/39 |
| 6,074,824 A * | 6/2000 | Hayashizaki et al. | 435/6 |
| 6,074,827 A * | 6/2000 | Nelson et al. | 435/6 |
| 6,180,417 B1 * | 1/2001 | Hajizadeh et al. | 436/518 |

FOREIGN PATENT DOCUMENTS

| | | | |
|---|---|---|---|
| EP | 0 284 232 | 10/2002 | |
| GB | 2 204 398 | 11/1988 | |
| WO | WO97/45742 | 12/1997 | .......... G01N 33/569 |
| WO | WO99/53093 | 10/1999 | ................ C12Q 1/68 |

OTHER PUBLICATIONS

International Search Report published with International Publication No. WO02/12895 on Feb. 14, 2002.
Dussan "On the Ability of Drops or Bubbles to Stick to Non-Horizontal Surfaces of Solids. Part 2. Small Drops or Bubbles Having Contact Angles of Arbitrary Size" *J.Fluid Mech.* 151:1-20 (1985).
Furmidge "Studies at Phase Interfaces. I. The Sliding of Liquid Drops on Solid Surfaces and a Theory for Spray Retention" *Journal of Colloid Science* 17: 309-324 (1962).

* cited by examiner

*Primary Examiner* — J. Hines
(74) *Attorney, Agent, or Firm* — Myers Bigel Sibley & Sajovec, P.A.

(57) ABSTRACT

The present invention concerns a method for the detection of an analyte in a droplet of fluid comprising the steps of providing a solid phase with a hydrophobic surface comprising at least one capture zone on which at least one binding agent with affinity for the analyte is immobilized, applying said droplet to the surface of said solid phase, applying a force that makes the droplet travel along the surface of said solid phase along a predetermined path thereby allowing the droplet to repeatedly contact said binding agent on the capture zone, applying conditions wherein said analyte is allowed to bind to said binding agent and detecting a complex of analyte and binding reagent at the position of the capture zone. The effect of a moving droplet is that the reactants in the droplet are well mixed which eliminates the risk of diffusion limitation. Such advantageous mixing is not obtained with conventional assays in which the surface is continuously exposed to the liquid. The use of a droplet eliminates the need for external mixing and also circumvents the need to dilute the sample in order to obtain sufficient volume to wet a large surface area.

16 Claims, 8 Drawing Sheets

MOVING DROPLET DIAGNOSTIC ASSAY

RELATED APPLICATIONS

Figure 1:
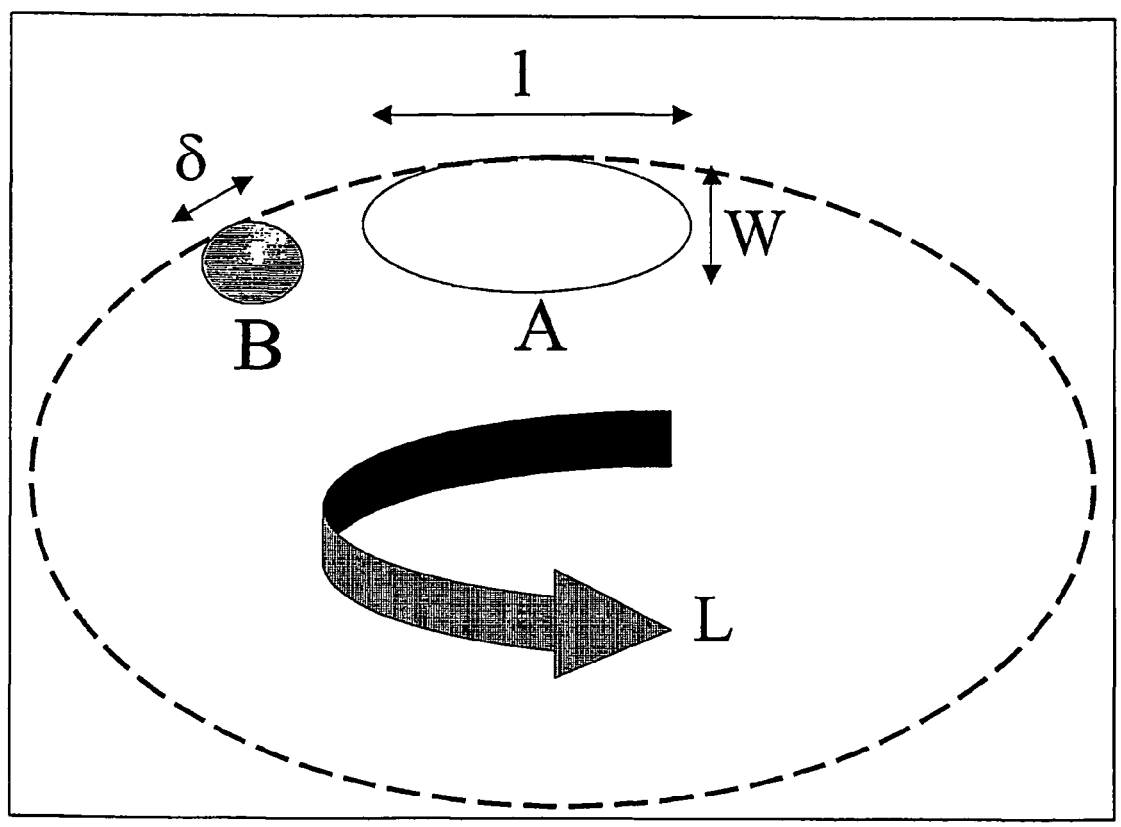

This application is a 35 U.S.C. §371 national phase application of International Application PCT/EP01/09073, filed Aug. 6, 2001 and published in English on Feb. 14, 2002, which claims priority to European patent application number 00202822.6, filed Aug. 10, 2000, the entire contents of each of which are incorporated herein by reference.

The present invention relates to a method for the detection of an analyte suspected to be present in a droplet of fluid.

Such methods are well known in the art of solid phase immunoassays. Immunoassays are available in a variety of formats. The quality of such assays is generally expressed in terms of the detection limit (the lowest concentration of analyte that can be measured) and the specificity (how certain is it that the response related to the analyte of interest and not to some similar agent). A third important performance parameter is the time and the effort that it takes for a user to obtain a test result. Especially for assays that are to be carried out by hand (non-automated systems or manual assays) it holds that the shorter the time required for the assay and the less interactions the better it is. A recent trend is to develop immunoassays for two or more analytes at the same time: ELISA assays that are sensitive to the presence of both antibody and antigen are commercially available, albeit that no discrimination can be made to whether the signal is generated by antigen or antibody.

Roughly, two classes of solid phase immunoassays are commercially available at the time: First, automated systems that are highly sensitive and specific, and with which large series of samples can be analysed. Such assays are often used in professional laboratories, include a variety of processing steps and require significant investments in infrastructure and personnel. Typical examples are microtiterplate-based ELISA assays. Secondly, manual assays are available, which are easy to operate ('dip-wait-and-read'), but usually do not meet the performance quality of the automated assays mentioned above. Home-use pregnancy and glucose assays are typical examples.

Consequently, there is a general desire in the art to improve the quality of manual assays with respect to the above mentioned parameters such as sensitivity, specificity and ease-of-use.

This desire has already lead to the development of a large variety of manual immunoassays. Roughly speaking, they can be divided into the following three groups, based on the physical principles on which they operate.

One group of solid phase immunoassays is based on the so-called flow-through principle. An example of a flow-through device is described in U.S. Pat. No. 4,632,901. In this device, antigen is immobilised on a first porous member and the analyte to be detected flows in a transversal direction through the porous member and is thereby for a short time in contact with the immobilised antigen. Liquid reagents containing the analyte are applied to one surface of the first porous member. The device also includes a second absorbent member in capillary communication with the surface of the first member opposite the surface where reagents are applied. The second absorbent member has capillary pathways aligned generally transverse to its upper and lower surfaces. The capillary pore size is selected to induce flow of liquid through the first member.

Another example of a flow through device is described in U.S. Pat. No. 4,920,046. This device contains improvements over the device described above, in that it employs a tracer comprising a particulate label which eliminates at least one step in the signal generation described in the '901 patent. Additionally the '046 patent describes how a skilled person may improve characteristics such as assay time and the number handling steps by carefully selecting the material for the test area.

A general disadvantage of the flow-through principle is the inefficient and uncontrolled use of sample material and assay reagents. Firstly, not all sample material and reagents pass the zone where the antigen is immobilised. Secondly, each analyte and reagent molecule pass the zone where the antigen is immobilised only once and reside there for a relatively short time, hence the immobilised antigen will only bind a portion of the available analyte. Another drawback is the lot-to-lot and within-lot variation in wicking characteristics of the porous member which contributes substantially to the variability of the test result. Yet another drawback of flow-through devices is that they are composed of a relative large number of components (often 10 or more), which contributes negatively to product consistency and manufacturing costs.

Another group of solid phase immunoassays is based on the so-called lateral-flow principle. Examples of lateral flow devices are described in Patent applications UK 2,204,398 and EP 0 284 232. The lateral flow format allows for a single step assay that requires only sample addition. In EP 0 284 232 a sample is added to one end of a porous carrier and migrates in a longitudinal way through the interstitial space of the porous carrier. While migrating along the porous carrier, the sample contacts and re-suspends a labelled specific binding reagent (e.g. colloidal gold, -selenium or -latex coated with antibody) which is dried on the porous carrier. The sample/label complex then continues to migrate to a capture zone of immobilised specific binding reagent, for instance an antigen. The sample/label complex will then bind to the specific binding reagent, thereby generating a visible read out at the position of the capture zone. Additionally, the '398 patent describes the lateral flow principle in combination with housing which makes the device also suitable for the layman.

One drawback of lateral flow devices is that they require relative large sample volumes because the sample is also used as washing fluid for the separation of reacted and non-reacted label. Another drawback of lateral flow devices is the heterogeneous release of the labelled specific binding reagent resulting into a significant variance of the eventually obtained signal. A drawback comparable to one observed in flow-through assays is the lot-to-lot and within-lot variation in wicking characteristics of the porous carrier, this can go up to 30%, and contributes significantly to the variability of the test result. Yet another drawback of lateral flow devices is the relative large number of components they are composed of, each having its lot to lot variability, which contributes negatively to product consistency and manufacturing costs.

A third group is formed by those solid phase immunoassays in which no active transport takes place of sample and labelled immuno-reactants. Examples of this group of immunoassays are described in U.S. Pat. No. 4,313,734, U.S. Pat. No. 4,373,932 and U.S. Pat. No. 4,703,017. In this type of assay, one binding agent is immobilised on an insoluble carrier, for example a plastic rod or the interior of a reaction vessel, and incubated with sample together with another, preferably labelled, binding agent. Separating the bound from unbound label takes place by physically separating the solid phase from the reaction mixture containing the unbound label.

One drawback of this type of immunoassays is the necessity to actively separate the bound from the unbound label before the end result can be measured. Another drawback is the need for relative long incubation times between the immobilised binding agent, sample and labelled binding agent due to the fact that the physical geometry hardly allows mass transport.

The above disadvantages are circumvented by the present invention, which concerns a method for the detection of an analyte in a droplet of fluid comprising the steps of
- providing a solid phase with a hydrophobic surface comprising at least one capture zone in which at least one binding agent with affinity for the analyte is immobilised
- applying said droplet to the surface of said solid phase
- applying a force that makes the droplet travel along the surface of said solid phase along a predetermined path thereby allowing the droplet to repeatedly contact said binding agent in said capture zone(s)
- applying conditions wherein said analyte is allowed to bind to said binding agent
- detecting a complex of analyte and binding reagent at the position of the capture zone.

Suitable solid phase materials are for instance glass, silicon or polymers like polystyrene, polyethylene etc. Preferably the solid phase material is non-porous and hydrophobic. If the solid phase material is not hydrophobic in its entirety, at least the surface to which the droplet is exposed should be hydrophobic.

Analytes that may be detected by this method encompass antigens, antibodies, haptens, nucleic acids, cells, membranes, bacteria or viruses.

A binding agent must have (direct or indirect) binding affinity to the analyte to be determined. Suitable binding agents are for instance antibodies, antigens, peptides, nucleic acids, polymers, or other specific reagents. These binding agents are to be immobilised on the hydrophobic surface by techniques well known in the art, such as, physical adsorption or covalent coupling or direct in situ synthesis or any other suitable technique.

Several, spatially separated capture zones may be applied on the same predetermined path. These capture zones may comprise the same binding agent or different binding agents. In case the same binding agent is applied in different surface concentrations or binding capacities, this may be used to quantitate the analyte concentration. In case different binding agents are applied, this may be used as an internal control or for the detection of different types of analytes. It is even conceivable to use many capture zones in an array-like manner. In this case it may be advantageous to have a small dimension ($\delta$) for each of the capture zones.

The complex of analyte and binding reagent at the position of the capture zone can be detected by methods well known in the art. Such methods may be based on visually detectable labels such as colloidal particles, particulate labels or other detectable labels. Especially suited for visual read-out are labels such as colloidal metal or polymer sols, carbon sols or dyes. Even more preferred are gold sol labels or latex labels. Other suitable labels—possibly introducing the need for instrumental read-out e.g. by electrochemical detection or by image analysis or other optical techniques—are enzymes or radioisotopes. The latter labels may also require additional assay steps and washing in between these steps.

The labelled component(s) may be provided in the form of a separate droplet and is placed in the predetermined pathway upstream or downstream to and preferably spatially separated from the capture zone(s). The labelled component(s) may also be added to the droplet of fluid suspected to contain the analyte to be determined. Alternatively it (they) may be provided as a hydrophylised reagent (to be dissolved or resuspended in the droplet fluid or to be added to the surface of the predetermined path way). Preferably the hydrophylised reagent may temporarily be fixed at a certain position on the hydrophobic surface of the predetermined pathway upstream or downstream to and preferably spatially separated from the capture zone(s).

The driving force to move the droplet along the predetermined pathway may be any suitable force which includes mechanical/electrical and manual force. Examples are respectively the use of low speed centrifugation or gravity. Obviously manual force is preferred in a simple test device ready to be used by doctors or patients; mechanical forces are obviously preferred in test laboratories, etc.

The effect of a moving droplet with its inherent limited volume and dimensions is that the reactants in the droplet are well mixed which eliminates the risk of diffusion limitation. Such advantageous mixing is not obtained with conventional assays in which the surface is continuously wetted and exposed to the liquid. The use of a droplet eliminates the need for external mixing and also circumvents the need to dilute the sample in order to obtain sufficient volume to wet a large surface area. More than one droplet may used in the above method. These droplets might even contain different analytes and/or labels.

The above advantages result in an improved assay performance by allowing rapid and reproducible testing. By keeping both analyte and reagents in a droplet, which means a volume that is 'as small as possible', the method allows to work at the highest possible concentrations of label and analyte, thus increasing binding rates and thus reducing assay time. Another advantage of low reagent and sample volumes is the intrinsically low cost price.

When the droplet contains all essential reagents, the concept of a migrating droplet has major advantages over a non-moving droplet. Not only the mixing as described above, but also in terms of readability. With the droplet on top of the binding agent, the contrast between free label in the droplet (solution or suspension) and the label material captured by the binding agent is low. Once however the droplet has moved away from the binding agent there is only a very small amount of free label in the residual droplet and an ever increasing amount of label bound to the binding agent in the capture zone. This may allow the user to monitor progress of the binding while the assay is carried out.

This implicit in-process bound-free separation gives this assay concept an even further advantage over existing solid phase immuno-assays. It is also possible to combine the method according to the invention with a suitable electro-optical detection system that—periodically—monitors the reflection or transmission at the capture zone(s).

In the method according to the invention, at least one specifically coated capture zone on a solid phase surface is periodically and repeatedly contacted with a droplet. The solid phase should consist of a hydrophobic material in order to maintain the shape of the droplet. The droplet, containing analyte and/or other reagents, has typical dimensions that are preferably small compared to those of the above solid phase. The droplet may move in one direction or back and forth preferably with constant speed over the above hydrophobic surface under the influence of a force, for instance gravity.

The physical and chemical properties of droplet and solid phase surface are of course—as the expert in this field may appreciate—important issues: for example the surface should be hydrophobic in order to keep the fluid compartment (droplet) intact.

It is to be understood that the droplet has to be small enough to be contained within the boundaries of the predetermined path, small enough to leave part of the path uncovered with fluid wherein said uncovered part is at least of similar dimensions as the capture zone. The mass of the droplet must be large enough to allow the droplet to move under the applied force. These conditions for the mass and volume of the drop will now be discussed in further detail.

When gravity is used as a force to move the droplet, it has been described in references 1 and 2 that the critical relation between the slope α of the surface, droplet's mass m and the liquid's advancing and receding contact angles $\theta_A$ and $\theta_R$ is given by:

$$mg \sin \alpha > w \cdot \gamma (\cos \theta_R - \cos \theta_A).$$

wherein g is the acceleration due to gravity (9.8 ms$^{-2}$) and w is the width of the droplet as measured orthogonally to the direction of motion (see FIG. 1).

This equation makes clear that when gravity is used as the driving force for the droplet the tilt angle α of the surface must be large for droplets that are small and/or show a large contact angle to the surface and—vice versa—can be small for large droplets on easily wettable surfaces. Too small contact angles, say smaller than 15°, introduce the risk of the droplet breaking up in smaller islands of liquid that no longer satisfy the above need for a large enough mass. For too large contact angles, say over 70°, it is possible that for volumes under 100 ul the droplet no longer moves since surface tension forces exceed gravity.

With reference to FIG. 1, the length L of the migration path of the droplet over the surface should preferably be large when compared to the length I of the droplet Typically, in order for the droplet to move easily under the force applied, the volume of the droplet is more than 10 ul, preferably more than 50 ul and even more preferably more than 150 ul whereas the volume of the droplet is preferably smaller than 1 ml, more preferably smaller than 0.5 ml in order to keep the droplet together and provide fast and efficient mixing.

For optimal mixing, it is also preferred to have an aspect ratio 1<l/W<100, even more preferably 1<l/W<10 for path lengths L (FIG. 1).

Figure 2:
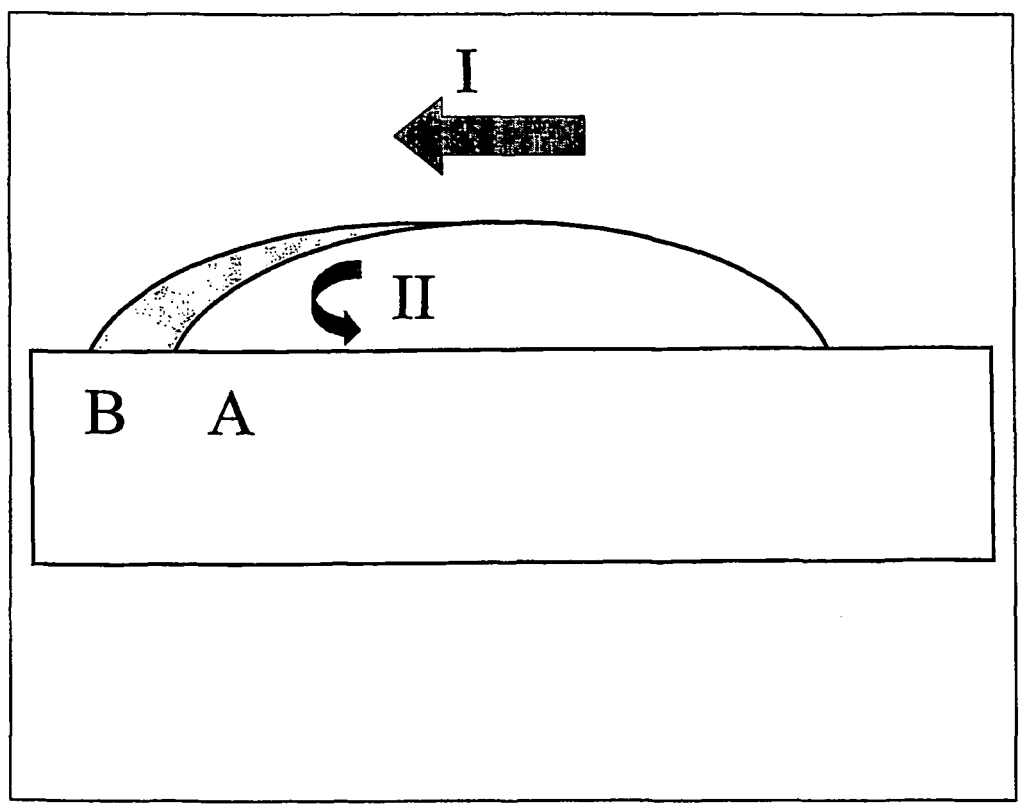

The ratio L/I should at least be larger than 1. It is advantageous to have a larger ratio L/I because the larger this ratio is the better the reagents are mixed in the droplet. During the continuous migration of the droplet the content is efficiently mixed, due to the internal rotation of the liquid upon transport (FIG. 2). However, the ratio L/I should not become too large because in that case the liquid film at the capture zone is not efficiently replenished, as will be detailed below. Therefore, a ratio of L/I smaller than 10 is preferred.

After the tail of the droplet has left the capture zone (FIG. 3), a thin layer (typically 5-15 micron) of the liquid remains on the surface of the capture zone due to adhesion. The reagents inside this layer continue to react with the binding agent on the solid phase. By the time the reagents become scarce due to depletion, they are replenished from the droplet that has continued its way over the path length L while mixing. Depleted reagents in the layer and fresh reagents from the droplet are exchanged and the reaction continues. The time T that is available for this exchange equals T=(L+δ)/v, with v being the average lateral velocity of the droplet. For a layer thickness that is typically in between 5 and 15 microns, and diffusion coefficients for immuno-chemicals in the order of 5.10$^{-11}$ m$^2$/s, T must be in the order of 0.1 to 5 seconds. This upper limit defines the maximum value of the ratio L/I that still makes sense with respect to rapid binding: As soon as the residual layer is depleted, signal build up stops. With the above relations, the acceptable range of possible dimensional relations between droplet, carrier geometry and motion properties can be determined and the sensitivity of the assay can be optimized.

A gutter may be used to define the predetermined path. With respect to the shape of the predetermined path it was observed that (FIG. 4) sharp angles should be avoided as such may enforce capillary action on the liquid and thereby keep a significant portion of the droplet from moving. Better should one use a smoothly shaped gutter geometry, with a curvature radius exceeding the droplet's smallest curvature radius by at least a factor 2 and even better by a factor 5.

Instead of a gutter, the predetermined path may be defined by a relatively hydrophylic path in a hydrophobic environment.

The lateral dimension δ of the capture zone where the binding agent is immobilized is preferably small compared to path length L, because it is advantageous to have the label concentrated on a relatively small surface area. The dimension δ preferably meets the following requirement:

$$\delta < \alpha L$$

wherein α<0.5 and preferably <0.1. The dimension δ should not be smaller than about 1 mm as to guarantee proper visual recognition.

In one embodiment of the invention as described in example 1, the bottom area of a polymer coffee cup was used as solid phase. On the edge of the circular bottom in a circumferential gutter one or two small areas were coated with a 20 microliter droplet containing an anti-hCG-antibody as the binding agent. After this specific coating at the capture zone the entire bottom of the beaker was incubated with a 50 ug/ml solution of BSA that acts as a blocking agent, A mixture of colloidal gold particles and hCG in a 150 microliter droplet was applied to the circumferential gutter and allowed to react with the immobilised binding agent. This experiment was done with and without rotating the beaker. Visual comparison of the colour intensity at the capture zone due to bound gold particles—a purplish spot—made unambiguously clear that the procedure using the migrating droplet resulted in a more sensitive assay. The results obtained with 10 and. 20 minutes without rotating matched those obtained using a rotating incubation for 2 and 5 minutes respectively. This proves that the rotating assay format accelerates reactions by at least a factor 4 to 5, and that this format allows very short incubations to obtain state of the art detection levels (20 IU/l of hCG).

The droplet fluid is not critical and may in principle be any liquid that can fulfil the conditions said above. Preferably, however, the droplet fluid suspected to contain the analyte to be detected is a droplet of human or animal body fluids or a droplet derived from human or animal body fluids such as urine, blood, plasma, serum, or spinal fluid. Also a droplet fluid containing one or more analytes derived or originating from human or animal body fluids or from any other suitable human or animal material such as cell or tissue material, including genetic material or amplified genetic material, obtainable by any possible chemical or other treatment, are preferred. The droplet fluid may, however, be taken from a totally different source as well without deviating from the gist of the invention, such as for example waste water that is to be inspected for particular specimen or an extract from food stuff that is to be monitored for the presence of a certain contamination.

Another embodiment of the invention is a device in which the above said method may be carried out.

The device according to the invention comprises a preferably non-porous, hydrophobic solid phase for receiving a droplet of fluid suspected of containing the analyte to be detected, said solid phase comprising a predetermined path way on its surface for repeatedly guiding the droplet along said path way, said path way comprising at least one capture zone in which a binding agent having direct or indirect affinity to said analyte is immobilised.

Such a device may comprise a predetermined path way that is shaped as a gutter. To even further improve mixing, the predetermined path way may be provided with at least one obstacle for instance shaped as a 'sleeping policeman'.

A further embodiment of the invention is a kit for performing the above described method, said kit comprising
- A device as described above
- Additional reagents necessary to perform the above method
- Instructions for use Additional reagents may be selected from the group consisting of suitable buffers, labelled reagents with affinity for the analyte that is to be detected, wash solutions, detergents, dilution reagents and positive or negative control reagents.

LEGENDS TO THE FIGURES

FIG. 1: Schematic representation of the geometric properties of the capture zone (B) with typical dimension δ and the droplet (A) with length I and width W. The droplet migrates over a predetermined path with length L FIG. 2: Schematic representation of a drop moving from A to B in direction I over a solid phase. During movement, the interior or the droplet is rearranged and effective mixing is obtained as indicated by II.

Figure 3:
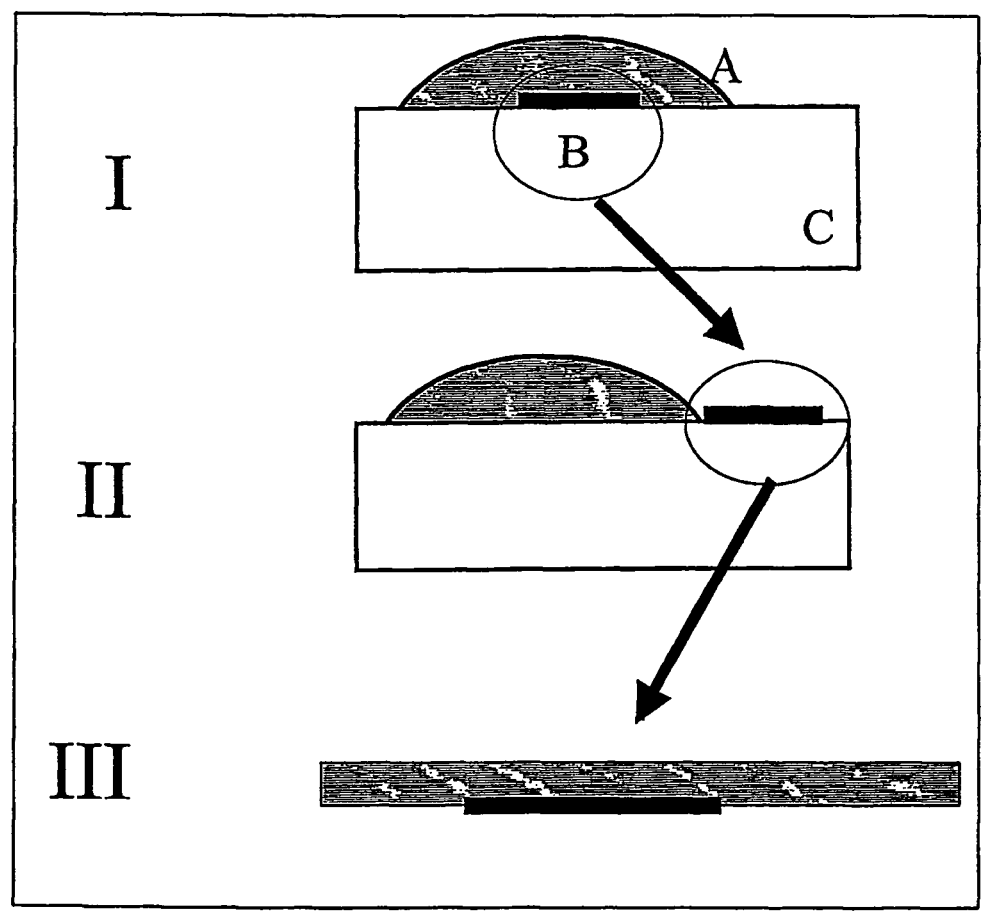

FIG. 3: Schematic representation of a drop (A) moving over a solid phase (C) comprising an immobilised binding agent at a capture zone (B). When the droplet covers the capture zone (I), the analyte is able to react with the binding agent. After passage of the droplet (II) a very thin layer of the liquid remains (III) and is replenished every time the droplet passes the capture zone.

Figure 4:
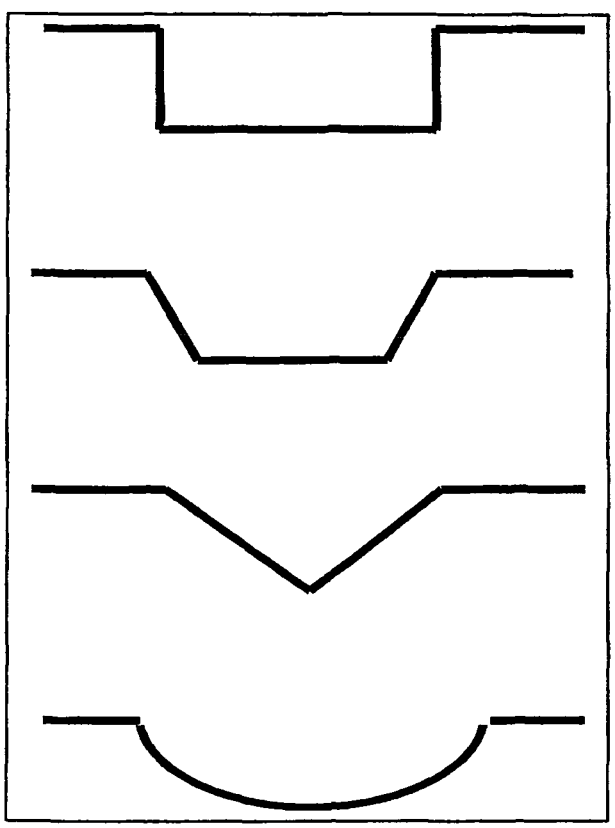

FIG. 4: Schematic representation of possible cross-section geometries of the predetermined path when shaped as a gutter. The upper three gutter geometries have sharp edges in which liquid remains due to capillary forces and is thus lost for further interaction. Shapes that resemble the lower—smoothly curved—gutter with a curvature radius exceeding the droplet's surface curvature radius were found to fully keep the droplet volume together.

Figure 5:
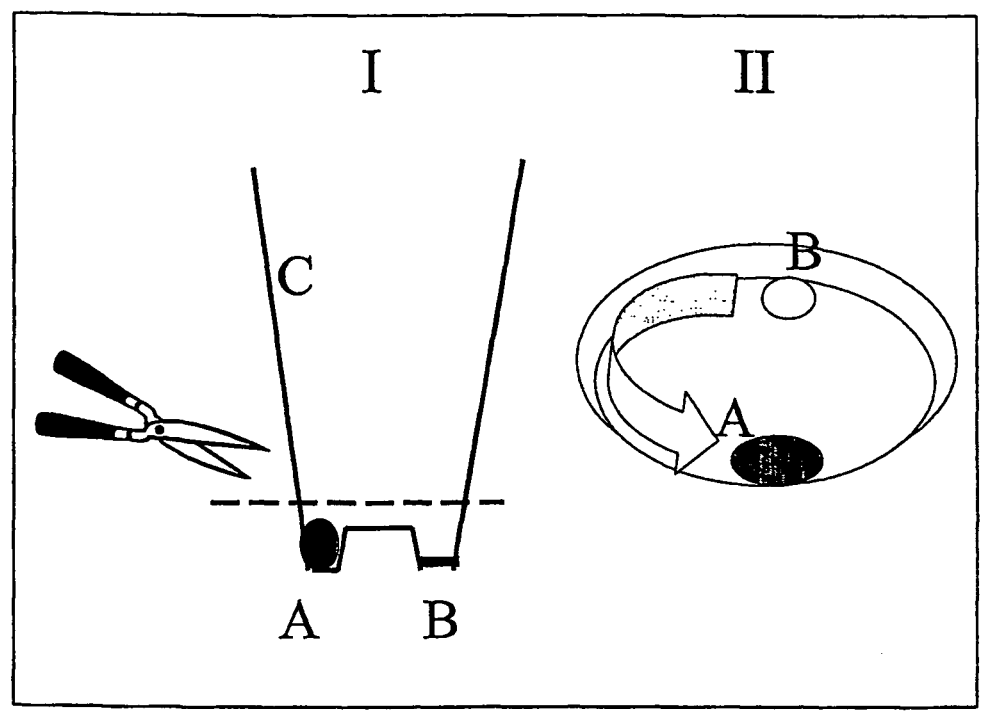

FIG. 5: An impression of the experimental set up of example 1: the bottom of a polymer coffee cup (C) was cut, and the circumferential groove was locally coated with an antibody against the human pregnancy hormone hCG to obtain a capture zone (B). After drying, a droplet of fluid (A) containing a mixture of hCG as the analyte and gold particles coated with ant-hCG as the label, was run along the circumferential groove. I: side view, II: top view.

Figure 6:
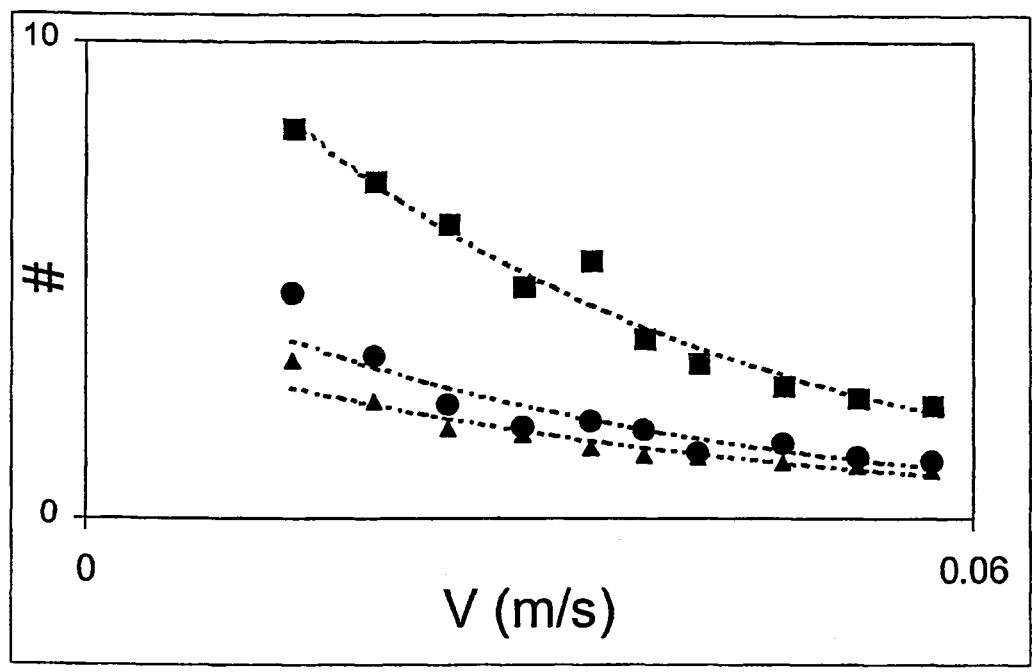

FIG. 6: Diagram showing the relation between the number of rotations (#) required for visually homogenising a 100 ul droplet as a function of the velocity V (m/s) of the droplet relative to the solid surface. Squares show the results obtained with a smooth bottom, circles represent the results obtained when a single disturbance ('sleeping policeman') is applied to the bottom surface and triangles when two of such disturbances are applied.

Figure 7:
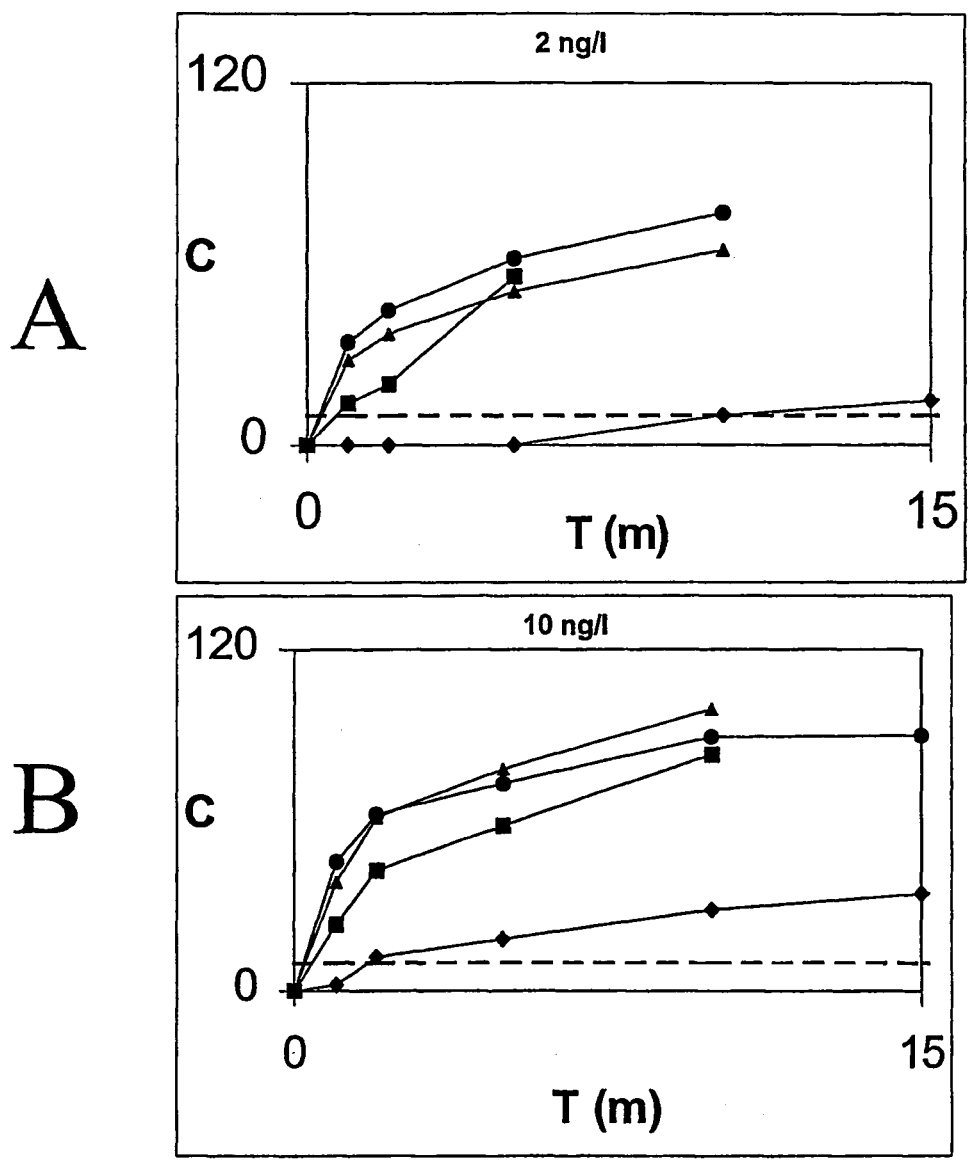

FIG. 7: Diagram showing the relation between the measured contrast C (capture zone versus background; expressed as grey value differences in a 8 bit image analysis system) and reaction time (T) in minutes (m). Upper diagram (A) shows the results for a hCG concentration of 2 ng/l, diagram (B) for 10 ng/l. Four different rotation speeds were applied: diamonds; no droplet motion, squares; 1 rotation of the beaker bottom per minute (RPM), circles; 3 RPM, and triangles; 6 RPM. The dashed line indicates the contrast level at which the human eye unambiguously experiences a 'positive' result.

Figure 8:
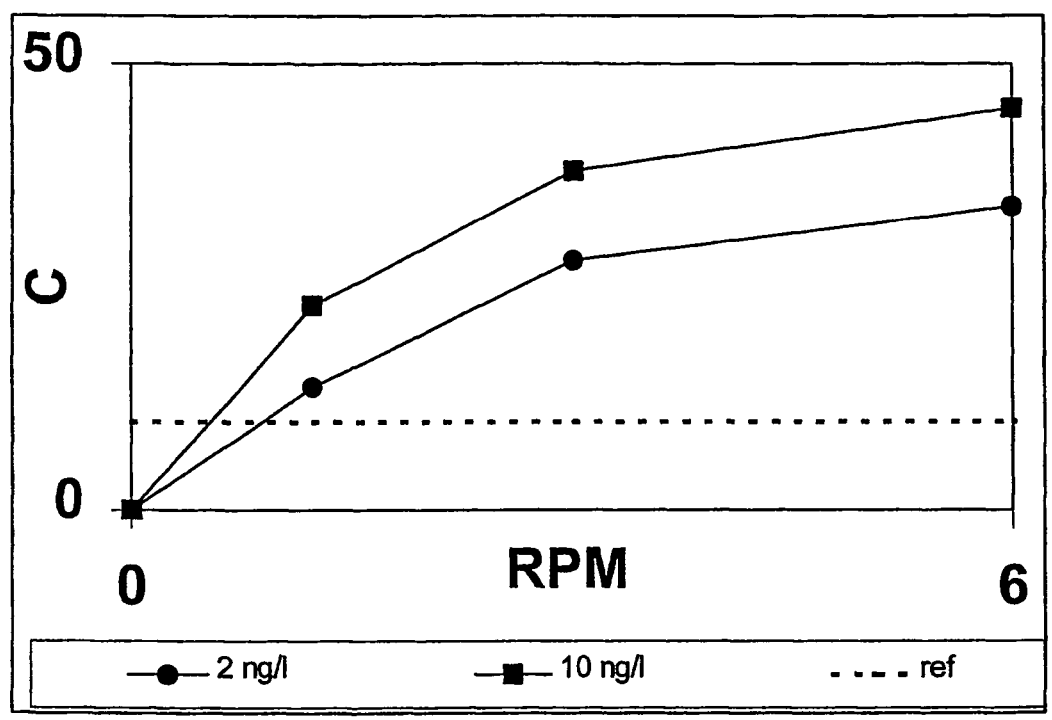

FIG. 8: Diagram showing the effect of the number of rotations per minute of the beaker bottom (RPM) on the measured contrast C between the capture zone and the background for two concentrations of hCG after 1 minute of reaction time (squares: 10 ng/l, circles: 2 ng/l). The dashed line indicates the contrast level at which the human eye unambiguously experiences a 'positive' result.

EXAMPLES

Example 1

Gold sols with an average particle diameter of 50 nm (A 540=5.0) were immuno activated according to Frens (Nature Physical Science Vol. 240, 1973, 20). In brief, a solution of 1 mg monoclonal hCG antibodies (beta-unit specific and prepared essentially as described in EP 045 103) per ml sodium chloride solution (9 μl) was adjusted to pH 8.0 using 0.1 M sodium hydroxide. One liter of the gold sol solution was adjusted to pH 8.0 with 0.1 M sodium hydroxide, mixed with 20 ml of the monoclonal hCG antibody solution and subsequently coated by adding 40 ml of a 20 M polyethylene glycol solution, pH 8.0. The coated gold sol labelled hCG antibodies were sedimented by centrifugation for 20 min. at 3500 g at ambient temperature. After removing the supernatant by suction, the gold sol pellet was resuspended to an A 540 value of 50.0 in a solution containing 2% (v/v) foetal calf serum, 160 g/L sucrose, 2% (w/v) Triton X100 and 1 M Tris, pH 8.0.

The bottom of a polystyrene coffee cup was used as a solid support. The circumferential groove of the bottom can function as a predetermined path for a droplet of fluid as indicated in FIG. 5A. Ten microliter of a 3 mg/ml monoclonal hCG antibody solution in sodium chloride (9 g/l, pH 8.0) was pipetted into the groove (FIG. 5A) and incubated for 30 minutes at ambient temperature. Next the discs were rinsed with de-ionised water and dried. Thus, a capture zone comprising a binding agent was created.

A reaction mixture was prepared by mixing 25 uL of the gold sol solution and 25 uL of a 25 mM Tris buffer (pH 8.0) spiked with 50 IU hCG/L. In one experiment the droplet of 50 uL reaction mixture was pipetted directly on the hCG antibody coated zone and incubated for 2, 5, 10 and 20 minutes, respectively (static incubation). The reaction was stopped by rinsing off the reaction mixture from the disc with de-ionised water. In a second experiment the same steps were performed as described in the first experiment, however now incubation took place by rotating the disc (dynamic incubation). The following results were observed:

TABLE 1

| Incubation time (minutes) | Static incubation | Dynamic incubation |
|---|---|---|
| 2 | − | + |
| 5 | +/− | ++ |
| 10 | +/− | +++ |
| 20 | + | +++ |

Example 2

Mixing studies made it clear that the time needed to homogenise the interior of the droplet (water with a small spike of a dye) reduced with increasing velocity of the droplet relative to the surface (FIG. 6). This is to be understood as the droplet to migrate like tumbling over causing an internal convection (FIG. 2). When one or two small vertical obstacles were introduced along the path of the droplet, mixing times roughly reduced by a factor 2 for each additional 'sleeping policeman' (FIG. 6)

Example 3

The influence of the rotation speed of the solid phase was investigated by rotating three solid phases as described in example 1 at three different speeds for 15 minutes. After recording the capture zone on videotape, the video frames were analysed using an 8 bit frame grabber to quantitate the grey value contrast between colored spot and the white polymer background. FIG. 7 shows the comparison of measured contrast values in time for three rotational velocities of the solid phase and for the motionless reference assay at two concentrations of hCG (A: 2 ng/l, B; 10 ng/l). Clearly, the threshold for visual perception (called REF) is exceeded significantly faster with a rotating droplet than in case of the motionless reference assay.

These experiments led to the conclusion that a moving droplet strongly reduces measurement time: 10 ngA gave a visually perceptible positive signal after only four rotations of the device.

REFERENCES

1. E. B. Dussan V. On the ability of drops or bubbles to stick to non-horizontal surfaces of solids. Part 2. Small drops or bubbles having contact angles of arbitrary size. J. Fluid Mech., 151:1-20, 1985
2. C. G. L. Furmidge. Studies at phase interfaces. I. The sliding of liquid drops on solid surfaces and a theorie for spray retention. J. Colloid Sci., 17:309-324, 1962

The invention claimed is:

1. A device for the detection of an analyte in a droplet of fluid, comprising:
   a non-porous and hydrophobic solid phase surface configured to receive and maintain the shape of a droplet of fluid;
   a circumferential gutter in said solid phase surface that defines a predetermined continuous pathway; and
   a capture zone located in the gutter;
   wherein said capture zone includes an immobilized binding agent positioned in said capture zone, said gutter configured such that when said droplet is positioned in said gutter and traveling along said pathway, said droplet repeatedly and periodically travels into and out of said capture zone.

2. The device of claim 1, wherein said gutter is provided with at least one obstacle.

3. The device of claim 1, wherein said gutter is circular.

4. The device of claim 1, wherein said circumferential gutter comprises a plurality of capture zones located in the gutter with each capture zone including an immobilized binding agent therein, the gutter being configured such that said droplet repeatedly and periodically travels into and out of said capture zone.

5. A kit comprising:
   a) the device of claim 1;
   b) reagents for detecting an analyte in the droplet of fluid; and
   c) instructions for use.

6. The kit of claim 5, wherein said gutter is provided with at least one obstacle.

7. A kit comprising:
   a) the device of claim 3;
   b) reagents for detecting an analyte in the droplet of fluid; and
   c) instructions for use.

8. A method for the detection of an analyte in a droplet of fluid, comprising the steps of:
   a) providing a non-porous and hydrophobic solid phase surface for receiving and maintaining the shape of said droplet, said surface comprising a circumferential gutter defining a predetermined continuous pathway and wherein a capture zone that includes an immobilized binding agent is positioned in said gutter;
   b) applying said droplet to said gutter;
   c) applying a force that makes said droplet travel along said predetermined continuous pathway of said gutter, wherein said droplet repeatedly and periodically travels into and out of said capture zone while maintaining a droplet shape, resulting in the formation of a complex of said analyte with said immobilized binding agent, further wherein the amount of complex increases as said droplet repeatedly and periodically travels into and out of said capture zone; and
   d) detecting said complex of analyte and binding agent in said capture zone, thereby detecting said analyte in said droplet of fluid.

9. The method of claim 8, wherein manual force is used to make the droplet travel along said predetermined continuous pathway of said gutter.

10. The method of claim 8, wherein the analyte is selected from the group consisting of antigens, antibodies, haptens, nucleic acids, cells, membranes, bacteria and viruses.

11. The method of claim 8, wherein the binding agent is selected from the group consisting of antigens, antibodies, peptides, nucleic acids and polymers.

12. The method of claim 8, wherein said gutter is provided with at least one obstacle.

13. The method of claim 8, wherein said gutter is circular.

14. The method of claim 8, wherein the force applied to make the droplet travel along said predetermined continuous pathway of said gutter is a gravitational force.

15. The device of claim 14, wherein the plurality of said capture zones comprise the same binding agent.

16. The device of claim 14, wherein the plurality of said capture zones comprise different binding agents.

* * * * *